(12) United States Patent
Martin Roth et al.

(10) Patent No.: US 7,555,356 B2
(45) Date of Patent: Jun. 30, 2009

(54) METHOD FOR MANUFACTURING A BODY-WORN ELECTRONIC DEVICE ADAPTED TO THE SHAPE OF AN INDIVIDUAL'S BODY AREA

(75) Inventors: Samuel Hans Martin Roth, Zurich (CH); Christoph Widmer, Wernetshausen (CH); Gregory Bleiker, Herrliberg (CH)

(73) Assignee: Phonak AG, Stafa (CH)

( * ) Notice: Subject to any disclaimer, the term of this patent is extended or adjusted under 35 U.S.C. 154(b) by 449 days.

(21) Appl. No.: 10/406,449

(22) Filed: Apr. 3, 2003

(65) Prior Publication Data

US 2004/0196995 A1 Oct. 7, 2004

(51) Int. Cl.
*G06F 19/00* (2006.01)
*H04R 25/00* (2006.01)
*A61B 7/02* (2006.01)
*H04R 5/00* (2006.01)

(52) U.S. Cl. .................. 700/118; 700/98; 181/129; 181/135; 381/23.1

(58) Field of Classification Search ............. 700/117, 700/97, 98, 118, 130, 132; 181/135, 130, 181/126, 129; 705/7, 26; 381/23.1
See application file for complete search history.

(56) References Cited

U.S. PATENT DOCUMENTS

| | | | |
|---|---|---|---|
| 4,611,288 A | | 9/1986 | Duret et al. |
| 5,487,012 A | * | 1/1996 | Topholm et al. ............ 700/163 |
| 6,401,859 B1 | | 6/2002 | Widmer et al. |
| 6,533,062 B1 | * | 3/2003 | Widmer et al. .............. 181/129 |
| 6,546,309 B1 | * | 4/2003 | Gazzuolo ..................... 700/132 |
| 6,665,577 B2 | * | 12/2003 | Onyshkevych et al. ...... 700/130 |
| 6,701,207 B1 | * | 3/2004 | Gazzuolo ..................... 700/132 |
| 6,772,026 B2 | * | 8/2004 | Bradbury et al. .............. 700/98 |
| 7,014,010 B2 | * | 3/2006 | Widmer ..................... 181/130 |
| 7,050,876 B1 | * | 5/2006 | Fu et al. ..................... 700/118 |
| 2002/0007294 A1 | * | 1/2002 | Bradbury et al. ............... 705/7 |
| 2004/0069560 A1 | * | 4/2004 | Widmer ...................... 181/135 |
| 2004/0107080 A1 | * | 6/2004 | Deichmann et al. ............ 703/6 |
| 2004/0243481 A1 | * | 12/2004 | Bradbury et al. ............. 705/26 |

FOREIGN PATENT DOCUMENTS

EP 1 246 506 A1 10/2002
WO WO 02/071794 A1 9/2002

OTHER PUBLICATIONS

Phonak: "NemoTech Digital Mechanical Processing" Information during 46th UHA Congress, Oct. 18, 2001, XP002249762 Stafa.
Thomas Wagner, Michael Boretzki: "Claro, ein Hörcomputer aus der Schweiz" Interview On Deutschlandradio, Feb. 11, 2002, XP002249763 Berlin, Retrieved from the Internet: <URL:www.dradio.de/cgi-bin/es/neu-patentes/170.html> retrieved on Jul. 29, 2003!

* cited by examiner

*Primary Examiner*—Crystal J Barnes Bullock
(74) *Attorney, Agent, or Firm*—Pearne & Gordon LLP (57) ABSTRACT

A body-worn device, such as a hearing aid, is adapted to the shape of an individual's body area, such as an ear. A digitized, three-dimensional representation of the area is prepared. At least one characteristic feature of the representation, such as a dimension of a part of the ear, is automatically determined. A shell is produced based on the characteristic feature. The body-worn device is assembled with the shell.

27 Claims, 6 Drawing Sheets

METHOD FOR MANUFACTURING A BODY-WORN ELECTRONIC DEVICE ADAPTED TO THE SHAPE OF AN INDIVIDUAL'S BODY AREA

The present invention is directed to a method for manufacturing a body-worn device, especially such electronic device which is adapted to suit the shape of an individual's body area.

Although the present invention departs from objectives as encountered in the art of hearing device manufacturing and especially hearing aid device manufacturing, as will become apparent to the skilled artisan, it may be used for more generalized manufacturing of body-worn devices, especially electronic devices, whereat the outer shape of such device shall fit to specific body's areas of an individual.

Therefore and without an intended limitation of the present invention to the art of hearing device manufacturing, the basic considerations which led to the present invention will be discussed with respect to hearing device manufacturing.

The process of manufacturing hearing devices, as especially hearing aid devices, thereby in-the-ear hearing aid devices, starts customarily by taking a cast or impression of the ear, thereby especially of the ear canal including parts of the outer ear. Traditionally by so-called "detailing process" the cast is roughly cut with respect to the type of device to be manufactured and the size and type of electronic components that will have to be placed in the device by assembling. In subsequent steps the cast is detailed by surface-machining and local or overall waxing allows for smoothening the surface, increasing the shape of the cast and fixing cast inaccuracies. The resulting detailed cast is used for making a negative to be used as a mold, wherein a shell of the device is produced using e.g. UV-curable material. After manufacturing of the shell, additional components as e.g. a vent is machined into the shell, holes are drilled for the receiver etc. and the resulting shell is finalized e.g. by grinding.

The device is lastly terminated by assembling electronic components into the shell.

Currently digital techniques become more and more involved in such manufacturing technique. With an eye on shell manufacturing attention is drawn to the U.S. Pat. No. 5,487,012 as well as e.g. to the WO 01/05207, WO 02/03756, U.S. application Ser. No. 09/670,207 and U.S. application Ser. No. 10/373,906, WO 02/24128 acc. to U.S. application Ser. No. 09/668,968 WO 02/25993 acc. to U.S. application Ser. No. 09/669,042 WO 02/24129 acc. to U.S. application Ser. No. 09/669,167 WO 02/25994 acc. to U.S. Pat. No. 6,484,842 WO 02/25995 acc. to U.S. application Ser. No. 09/669,169 WO 02/24127 acc. to U.S. Pat. No. 6,401,859.

The accuracy and adequateness of the addressed manual detailing of casts is mainly a question of experience and individual preference of the skilled artisan performing such detailing for an individual's body area. While high experience allows for more efficient and reliable detailing the process is still prone to errors and to very little reproducibility. In test series several shell makers have been given identical casts and orders for the device to be manufactured and have been asked to produce the corresponding shell. The results have been vastly different both in size and shape, a clear indication of missing reproducibility and personal disagreement on optical shape represented by the cast. Overall such differences in the detailing process contribute to an average industry return rate, in the field of hearing aid devices, of 16 to 21%.

It is an object of the present invention to deal with drawbacks of the addressed manufacturing technique. This is achieved by manufacturing a body worn device, especially electronic device, which is adapted to the shape of an individuals' body area and which comprises the steps of
  preparing a digitized, three-dimensional representation of individual's body area;
  automatically determining at least one characteristic feature of the representation;
  producing a shell in dependency of said at least one characteristic feature;
  assembling said device with said shell.

Accordingly, there is provided by the present invention a method for manufacturing a shell for a body-worn device adapted to the shape of an individual's body area, which comprises all the said steps except the step of assembling the device with the shell.

By automatically determining the at least one characteristic feature of the digitized representation, information is provided of such characteristic feature as a basis for producing a shell. Because such determining is automatically performed reproducibility is improved. Finding of such characteristic features at the representation is not anymore subject to operator's expertise and personal preferences, In a most preferred embodiment of the manufacturing method according to the present invention, it further comprises the step of detailing the digitized representation in dependency of the at least one characteristic feature as automatically determined and producing the shell in dependency of the detailed digitized representation. Thereby, the determined characteristic feature is an accurate basis for deciding how and where the digitized representation is to be detailed, so that again reproducibility of the detailed digitized representation and thus of the resulting shell is significantly improved.

In a further preferred embodiment detailing comprises at least one of cutting, surface treating, offsetting, fixing, relaxing and increasing at least a part of the digitized representation, whereby such actions are performed digitally.

In a further preferred embodiment the step of automatically determining the at least one characteristic feature comprises performing such determining by automatically investigating the digitized representation under the constraint of predetermined geometrical rules. Thereby, e.g rules with respect to curvature, surface areas of cross-sections, etc., of the digitized representation are investigated under predetermined criteria so as to find at the digitized representation the location of the respective characteristic feature.

In a further preferred embodiment the determining step comprises comparing the digitized representation with a digital representation of a standard of the body area. Thereby, both approaches, namely that of performing determining with automatic investigation under the constraint of predetermined geometrical rules and by performing a comparison are combined. For instance it is by performing such comparison that it is easily established whether a digitized representation as provided is accurate enough or not. If e.g. a difference found by such comparing exceeds a predetermined level, there is at least a high degree of likelihood that the digitized representation does not represent individual's body area with an accuracy high enough. Further, if the actually treated digitized representation is close enough to the standard, characteristic features of the standard may be exploited as the respective characteristic features of the digitized representation actually treated and may thus be taken at least as a first approximation of such characteristic features to be automatically determined at the digitized representation.

In a further embodiment according to the present invention the step of preparing the digitized representation is performed by scanning a cast of the body area. In a further preferred embodiment the step of preparing the digitized representation is performed by three-dimensional scanning of the body area directly.

As a further embodiment of preparing the digitized representation that step comprises providing such representation of the body area as one which has already been applied for manufacturing a body-worn device and which shall e.g. be improved, taking into account needs of the individual which have changed since the body-worn device had been manufactured. Such changing needs may be based e.g. on individual's growth, aging, etc.

In a further preferred embodiment of the manufacturing method according to the present invention the step of preparing the digitized representation is performed by scanning a cast of the body area, whereby detailing comprises mechanically detailing the cast in dependency of the detailed digitized representation, thereby producing the shell from said mechanically detailed cast. In this case the detailed digitized representation provides for information how to mechanically detail the cast.

In a further preferred embodiment mechanical detailing of the cast is performed by digitally controlled treatment or machining.

If e.g. due to a material selected for manufacturing the shell mould production of the shell is preferred and in a further embodiment it is the mould which is produced in dependency of the detailed digitized representation. In spite of the fact that such mould producing may still be performed manually and based on the information from the detailed digitized representation, in a preferred mode such mould production is performed by a digitally controlled process, which is digitally controlled dependent from the detailed digitized representation.

Nevertheless, in a most preferred embodiment production of the shell is performed directly by means of a digitally controlled process, whereby such process control comprises controlling by the detailed digitized representation.

As has been discussed above, in a preferred embodiment the method according to the present invention comprises detailing the digitized representation in dependency of the at least one characteristic feature as determined. Departing therefrom and in a most preferred embodiment the method according to the present invention comprises the step of providing automatically at least one of detailing and of at least one suggestion for performing said detailing. By automatically performing detailing and/or by automatically providing a suggestion how to perform detailing at the digitized representation, reproducibility is again significantly increased and such detailing action becomes significantly less dependent on personal expertise and personal preferences of an operator.

In a most preferred further embodiment the step of automatically providing at least one of detailing and of at least one suggestion for such detailing is performed on the basis of an expert system and of at least one predetermined target to be achieved. As one and the same digitized representation may be used for constructing different devices, it is important at least for some detailing steps to specify, which device shall be manufactured. Let's take a digitized representation of the outer ear and ear canal, such digitized representation may be used for manufacturing an outside-the-ear device OTE, an in-the-ear device ITE or a completely in-the-canal CIC device, which devices obviously necessitate different derailing at the one digitized representation.

In a preferred further embodiment such expert system is based on pre-established geometric rules and/or on recorded knowledge.

In context with established or recorded expert knowledge a preferred generic embodiment of the method according to the present invention is to check accuracy of the prepared digitized representation and/or of the automatic determination of at least one characteristic feature by comparing the digitized representation and/or the at least one characteristic feature as determined respectively with a standard digitized representation and/or a standard characteristic feature.

In a further most preferred embodiment providing automatically at least one of detailing and of at least one suggestion comprises comparing the digitized representation with more than one digitized representations as approved to be accurate so as to find that approved digitized representation which best matches with the digitized representation as actually treated. There is generated the detailing step and/or said suggestion in dependency of the detailed digitized representation of the best matching digitized representation.

In a further preferred embodiment the expert system is continuously updated in dependency of the detailed digitized representation actually treated, if latter reveals to be approved after producing the shell. Thereby, such approved detailed digitized representation is added to the further approved digitized representations for finding the best match so as to update comparison basis for such finding.

If the device to be manufactured is a hearing device and the individual's body area comprises the ear canal, the characteristic feature is preferably one of
end of ear canal
entrance of the ear canal
medial axis of the ear canal
first canal bend
second canal bend
left ear canal
right ear canal
horizontal line.

If individual's body area comprises the outer ear area adjacent to the ear canal the characteristic feature is preferably one of
tragus
anti-tragus
inter-tragal notch
concha
crus
helix
left ear
right ear
horizontal line In a most preferred embodiment the device manufactured is a hearing device, thereby, further preferred, an in-the-ear hearing device. Nevertheless, such a device may also be an outside-the-ear hearing device.

In a still further embodiment the addressed devices are hearing aid devices.

In a still further preferred embodiment of the method according to the present invention, the detailed digitized representation data is stored in the device as manufactured.

A system according to the present invention for manufacturing a shell for a body-worn device comprises a storing unit for a data set representing a three-dimensional image, a processing unit, the input thereof being operationally connected to an output of the storing unit, whereby the processing unit generates at its output automatically a changed data set departing from said data set.

Preferred embodiments of the invention shall now be further described to the skilled artisan making reference to figures.

Figure 1:
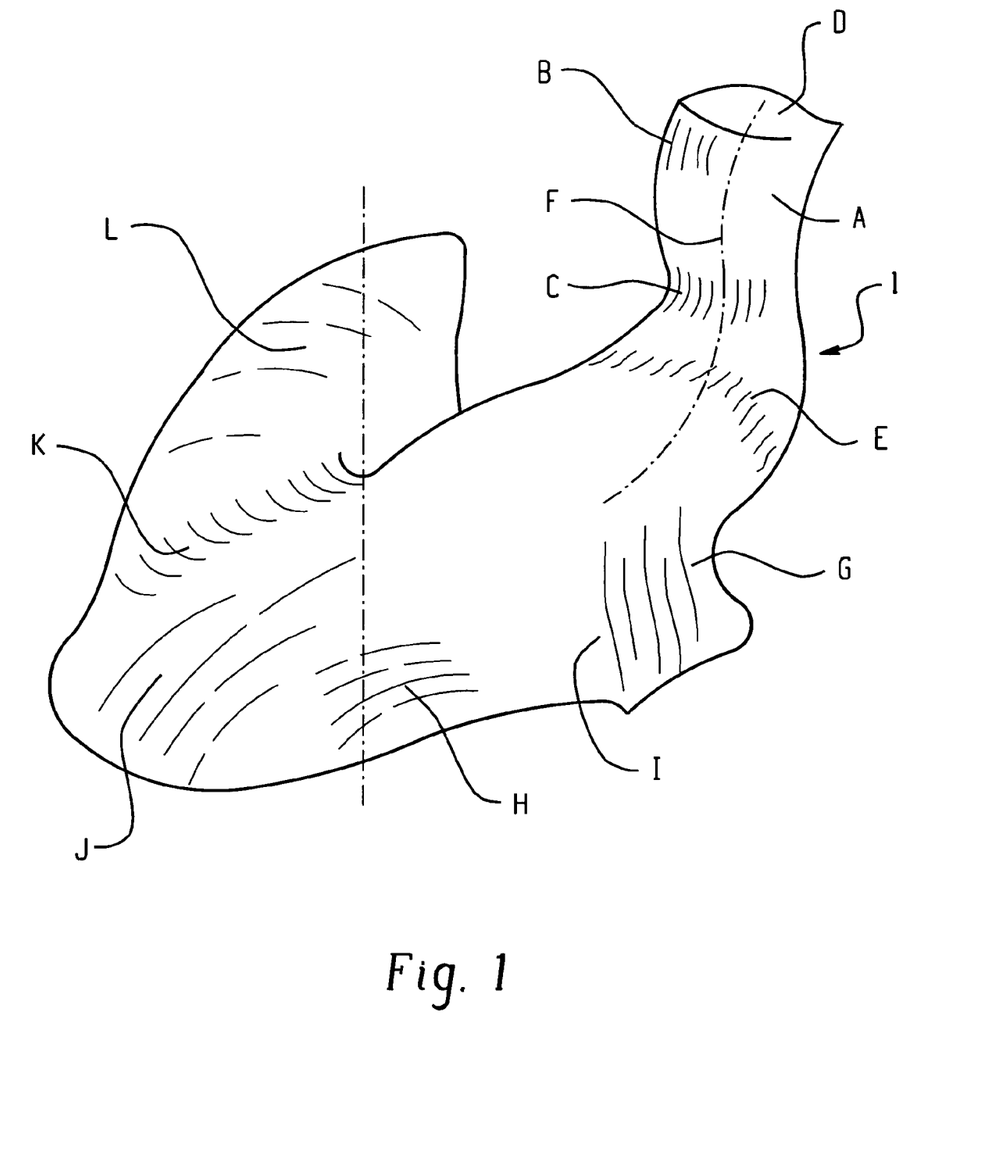
FIG. 1 in a perspective representation and as an example of an individual's body area, a digitized representation of the outer ear and canal area to define characteristic features.
Figure 2:
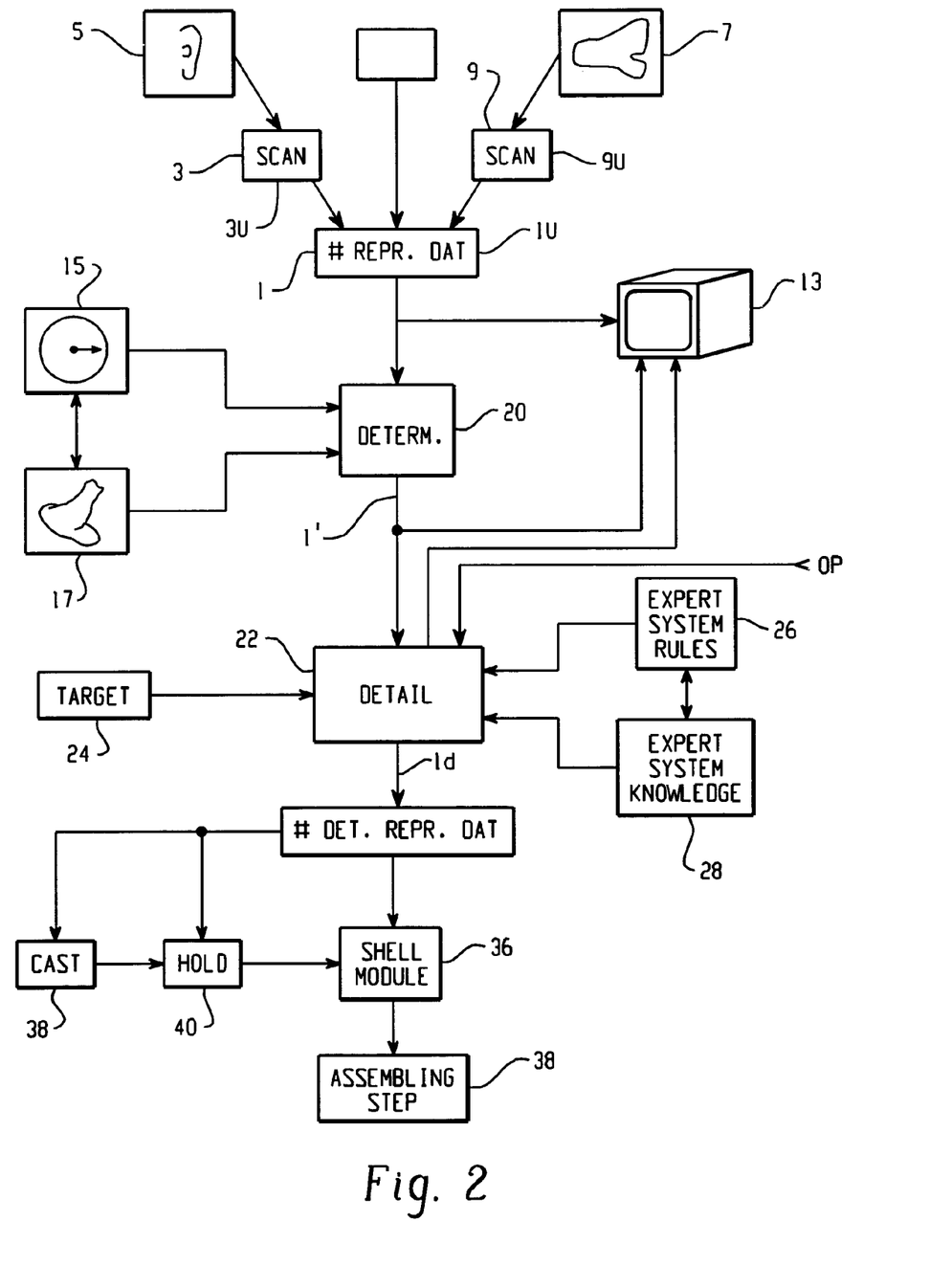
FIG. 2 in a flowchart and functional block/signal-flow diagrammatic representation, a preferred embodiment of a system according to the present invention operated to perform the manufacturing method according to the present invention.

In FIG. 1 there is shown in a perspective schematic view a digitized representation 1 from the outer ear and ear canal of an individual as a most preferred example of an individual's body area, whereat a device to be manufactured shall be applied. Characteristic features of such representation are e.g.:

A: canal
B: second bend
C: first bend
D: end of canal
E: entrance of canal
F: center line representing medial axis of the ear canal
G: tragus
H: anti-tragus
I: inter-tragal notch
J: concha
K: crus
L: helix
M: horizontal line, when the cast 10 resides in individual's ear In FIG. 2 there is shown by means of a simplified flowchart or signal-flow/functional block representation a preferred embodiment of the method and system for manufacturing according to the present invention.

There is prepared a digitized three-dimensional representation 1 of the area of interest of individual's body. This representation 1, e.g stored in a storing unit 1U, is in one embodiment prepared by performing a three-dimensional scan 3 by a scanner unit 3U of the area 5, e.g. of the outer ear and ear canal area 5. Alternatively there is made a cast 7 of individual's area of interest, which is then scanned—9—by a scanner unit 9U to result in the three-dimensional representation 1. Still alternatively the three-dimensional representation 1 may be provided from an earlier digitized three-dimensional representation of that area, which earlier representation shall be changed, e.g. updated. With an eye on ear canal representation this may become necessary with increasing age of the respective individual.

Figure 3A:
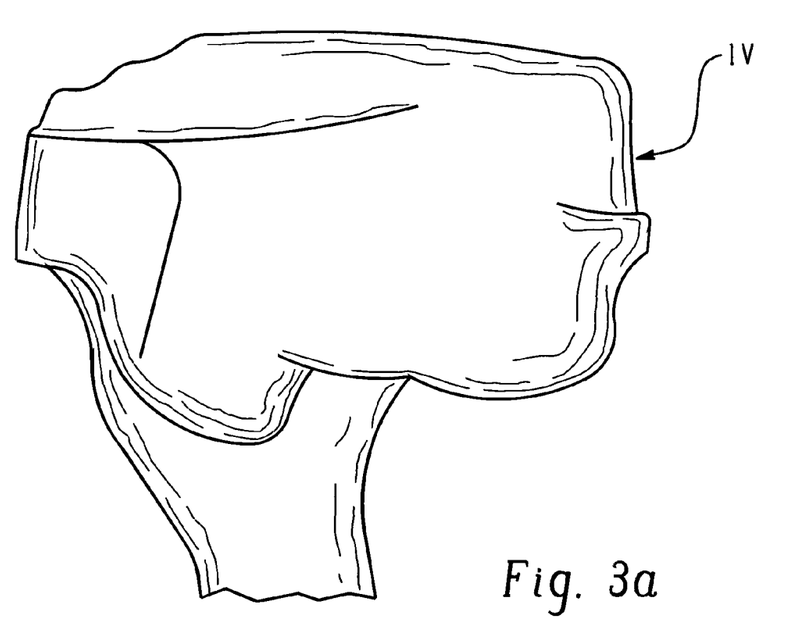
FIG. 3a visualized and as an example a digitized representation of outer ear and of a part of the ear canal.
Figure 3B:
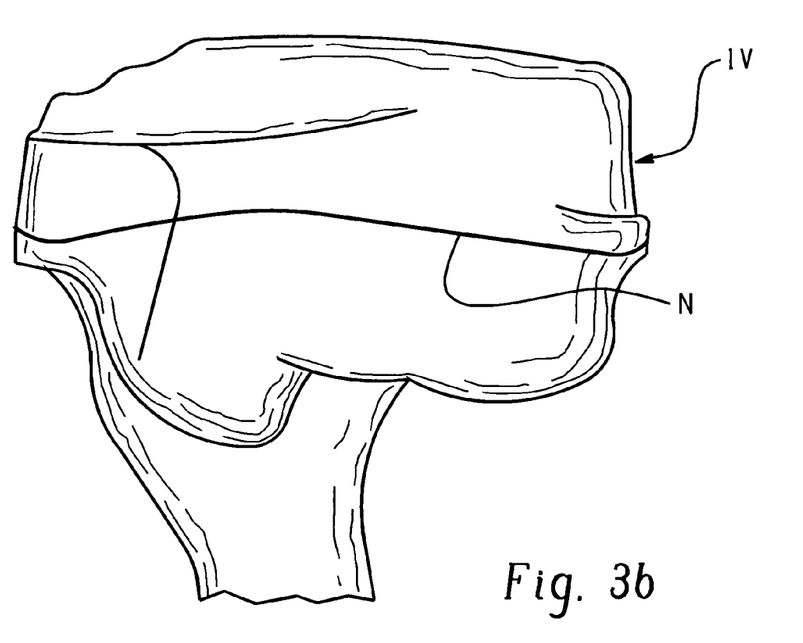
FIG. 3b departing from the visualized digitized representation as of FIG. 3a, a visualized digitized representation after applying an enveloping surface.

Visualized (V) on a computer display 13 as of FIG. 2, the digitized representation 1 of the outer ear and part of the ear canal is shown as an example in FIG. 3a resulting by computerized applying an envelope surface, in a representation according to FIG. 3b. The digitized representation 1 is the basis for automatically determining at least one characteristic feature thereat. Such characteristic features are found by applying predetermined geometric rules 15 to the digitized representation 1, thereby investigating the digitized representation data 1 with the constraint of such rules. For instance and with an eye on the digitized and visualized representation 1V according to the FIGS. 3a and 3b and as shown in FIG. 3b, an outermost in-plane contour line N is detected in the digitized representation 1 e.g. as the contour, along which the outer surface of the digitized representation 1 starts bending inwardly, as an example of a very simplified rule to find contour N. With respect to addressed example of an individual's body area of interest, namely of a digitized representation 1 of outer ear and ear canal, a further characteristic feature of importance is the centre line or medial axis of the ear canal and part of the outer ear. This line is e.g. established by calculating the centre point $P_{C_N}$, i.e. the centre of weight of the plane-surface $W_N$ defined by the in-plane contour N. Parallel equidistant slices to $W_N$ are computed from the digitized representation 1 and the respective centre points $P_{C_X}$ define concomitantly the centre line F up to reaching the end D of the ear canal representation. This is schematically shown in the visualized digitized representation 1V in FIG. 4 by centre line F linking centre points $P_{C_m}$, $P_{C_n}$ . . . of slices n, m . . . .

Whereas in a first run to find a first approximation of centre-line F the slices, whereat the centre points $P_{C_X}$ are calculated, are e.g. established parallel to the plane of surface $W_N$. In a second run the slices are angularly adjusted to be in planes perpendicularly to the first approximation of the centre line F yet found. This results in slightly shifted centre points, which thus define for a second approximation of the centre line F. By such approach and iterative looping a high degree of accuracy for the course of the centre line F in the digitized representation 1 is achieved.

Figure 4:
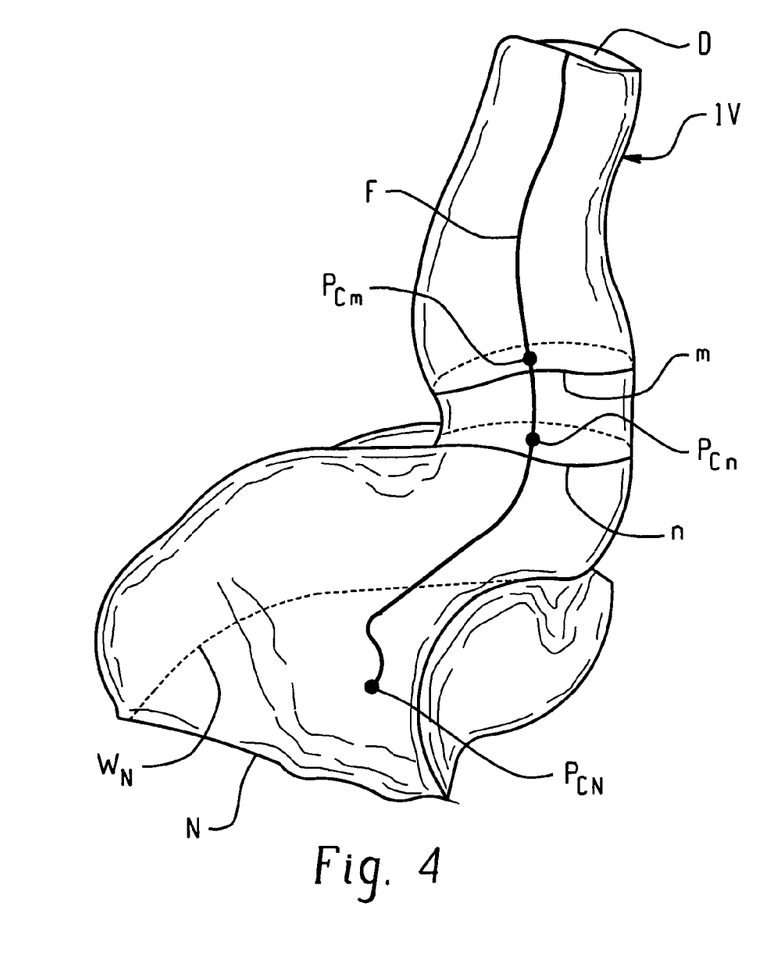
FIG. 4 a visualized digitized representation with automatically determined characteristic features.
Figure 5:
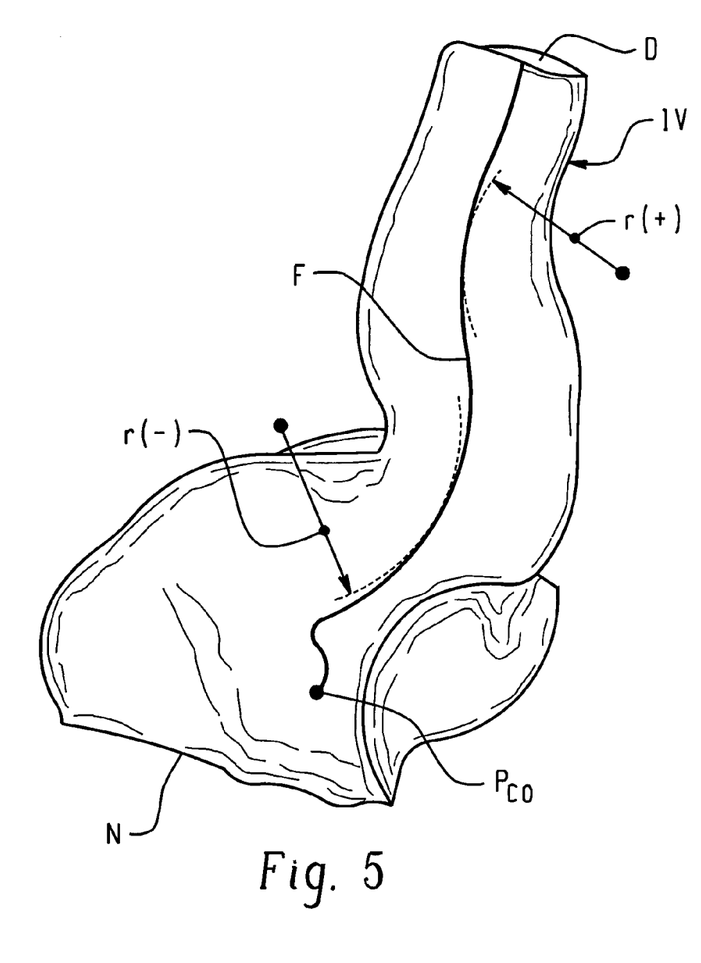
FIG. 5 in a representation in analogy to that of FIG. 4, additional characteristic features as determined automatically according to the present invention.

As a further characteristic feature e.g. first and second bends of the ear canal at the example addressed may or will be automatically determined. To do so, e.g. an analysis of curvature of the centre line F as of FIG. 4 is performed in combination with an analysis of the outer surface of the digitized representation 1 and thereby especially its curvature, especially in direction of the centre line. A simplified rule for determining the first and second ear canal bends is the change of signum of curvature of the centre line F as schematically shown in FIG. 5 with respectively directed curvature radii $r_T$ and $r_-$.

Figure 6:
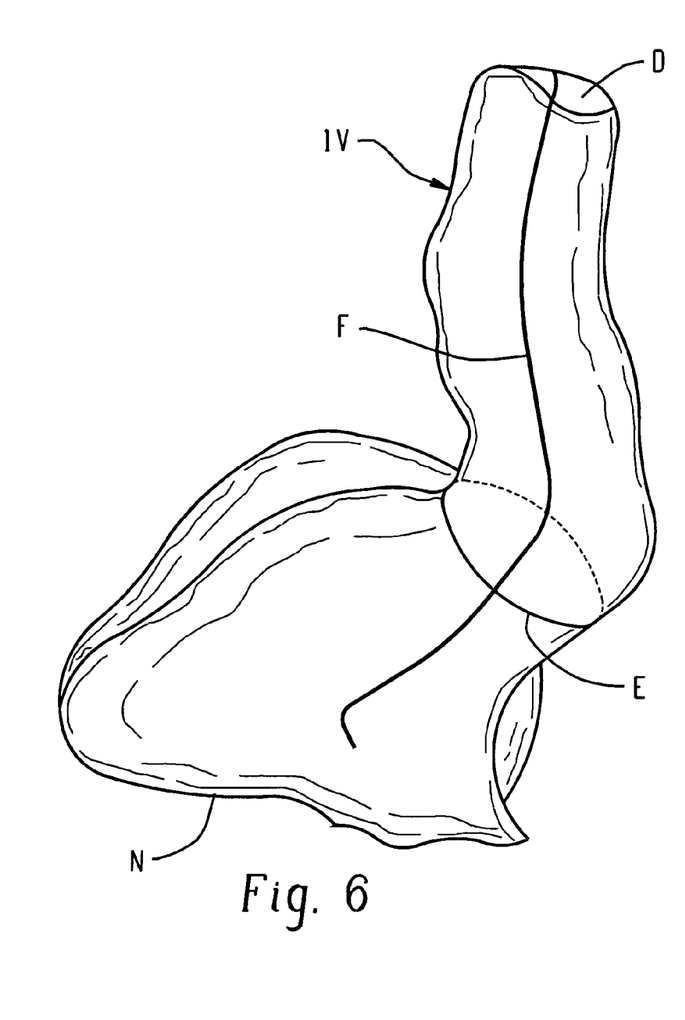
FIG. 6 still in analogy with the representations of the FIGS. 4 and 5, location of a still further characteristic feature automatically determined.

As a further feature of interest the aperture plane, whereat the ear canal starts departing from the outer ear is or may be computed by analyzing the sequence of slices perpendicularly and along the centre line F and following the rule that the surface area of such slices in direction from the ear canal towards the outer ear significantly increases there, where the aperture plane E is to be located. As shown in FIG. 6 such an analysis following such a rule results in the finding of the entrance of canal plane E.

Whereas as described up to now the characteristic features are automatically determined by investigating the digitized representation 1 according to predetermined geometric rules 15, a further possibility to find such characteristic features is to compare the digitized representation 1 with digitized representation 17 according to FIG. 2 of same area of individual's body, which has been approved and established as a standard of a digitized representation of individual's body area. By comparing the prevailing digitized representation 1 with the established standard representation 17 at least a first approximation of localizing the characteristic features as mentioned above at the digitized representation 1 under investigation is achieved. In a preferred embodiment both possibilities, namely of determining the characteristic features based on rules 15 as well as based on a comparison with a standard 17 are performed. Thereby latter may especially lead to a conclusion, whether the characteristic features as determined based on rules 15 have a good likelihood to be correct or not and thereby may reveal e.g. an inaccurate establishment of the digitized representation 1, e.g. due to inaccurate scanning 3, 9, or inaccurate casting 7.

From the step 20 according to FIG. 2 of determining automatically the characteristic features, or at least one thereof, at the digitized representation 1 there results such a digitized representation 1 with the recognized or determined characteristic features thereat. This is schematically shown in FIG. 2 by the outcome of determining step 20 as a digitized representation 1' incorporating determined characteristic features. This "featurized" digitized representation 1' is e.g. visualized as shown in FIG. 2 at display 13, leading e.g. to visualized representations according to FIGS. 3b to 6. Further characteristic features as location of end of canal, tragus, anti-tragus, inter-tragal notch, concha, crus, helix and horizontal line are determined in analogy to the features exemplified above, based on applying geometric rules and/or based on comparison with a standard digitized representation, whereby such geometric rules are based e.g. on surface curvature analysis, centre line analysis, etc.

As was mentioned above the digitized representation 1' does not differ from the digitized representation 1, but incorporates the localized characteristic features, i.e. additional, automatically found information.

With this digitized representation 1' as an input there is most preferably performed a detailing step 22. By such detailing the digitized representation 1 is principally changed. Such change is performed based on the additional information as provided by the determined characteristic features. Some of the detailing actions will be unspecific to predetermined targets 24. As an example one customarily performed detailing action will be to perform a cut at the digitized representation 1' along the contour N according to the FIGS. 3b to 4.

By predetermining target or targets 24 it is established e.g. what type of device is to be manufactured.

Detailing the digitized representation 1' may thereby preferably comprise at least one of digitally cutting, surface treating the digitized representation 1', offsetting locally parts thereof, fixing parts thereof having been detected as inaccurate, e.g. by comparing with standard 17 as explained above, relaxing the digitized representation.

The detailing step 22 is preferably performed automatically and/or in dependency of automatically provided detailing suggestions to the operator.

Such suggestions—which are automatically followed, if automatic detailing is performed—on how to change the representation 1' are automatically generated on the basis of an expert system 26, 28. The expert system preferably comprises on one hand geometric algorithms and rules 26 applied to the digitized representation 1' in view of a given target and/or on the other hand established knowledge 28. Based on such suggestions, preferably visualized as shown in FIG. 2 at the display 13, the detailing action is nevertheless preferably operator-controlled, OP. The operator may select to fully follow the automatically provided suggestion or may, as an expert, more or less depart from such suggestion. E.g. if the target 24 established in the specific example discussed, namely of manufacturing an ear-applicable device, thereby especially a hearing device, is to manufacture a complete in-the-canal hearing device CIC, one target-related rule 26 is e.g. based on the fact that such a CIC device is to be placed deeply into the ear canal, reaching clearly beyond the first and up to nearly the second bend C, B, according to the definitions given in context with FIG. 1.

Thus, an automatically provided suggestion or an automatically performed action could be to cut the digitized representation 1' just upstream the first bend and just upstream the second bend. Additionally, the characteristic feature "aperture plane" as of E of FIG. 6 gives a further basis for the outermost cutting of the digitized representation 1' e.g. as a function of a further target 24, namely of what kind of a face-plate module is to be provided at the device to be manufactured.

By operator's action OP modules to be incorporated in the device to be manufactured are digitally localized at or within the digitized representation 1' and there is performed an automatic evaluation, where such modules are best located within the digital representation 1', taking e.g. further targets into account, as e.g. predetermined thickness of a shell module for the device. There is performed automatic moving of the modules in and along the digitized representation 1' to automatically provide detailing actions and/or a suggestion or suggestions for geometrically arranging such modules, tailoring the shell module, so that there occurs no module-collision.

Additional targets are preferably considered, e.g. least visibility of the CIC from outside, taking different viewing angles into consideration.

The detailing actions are performed at the digitized representation 1', whereby preferably the operator OP may interact with such detailing by possibly performing such detailing, as was outlined above, more or less differently than automatically suggested.

Thus, following the above example of CIC manufacturing as a target 24, there will be a cut of the digitized representation according e.g. to the preferred face-plate location, adjacent to the ear canal opening plane E and a cut adjacent the second bend B according to FIG. 1. Further preferably digital "machining" of an interior space of the digitized representation 1' is automatically performed or suggested for optimally applying modules as necessitated by the target device.

Figure 8:
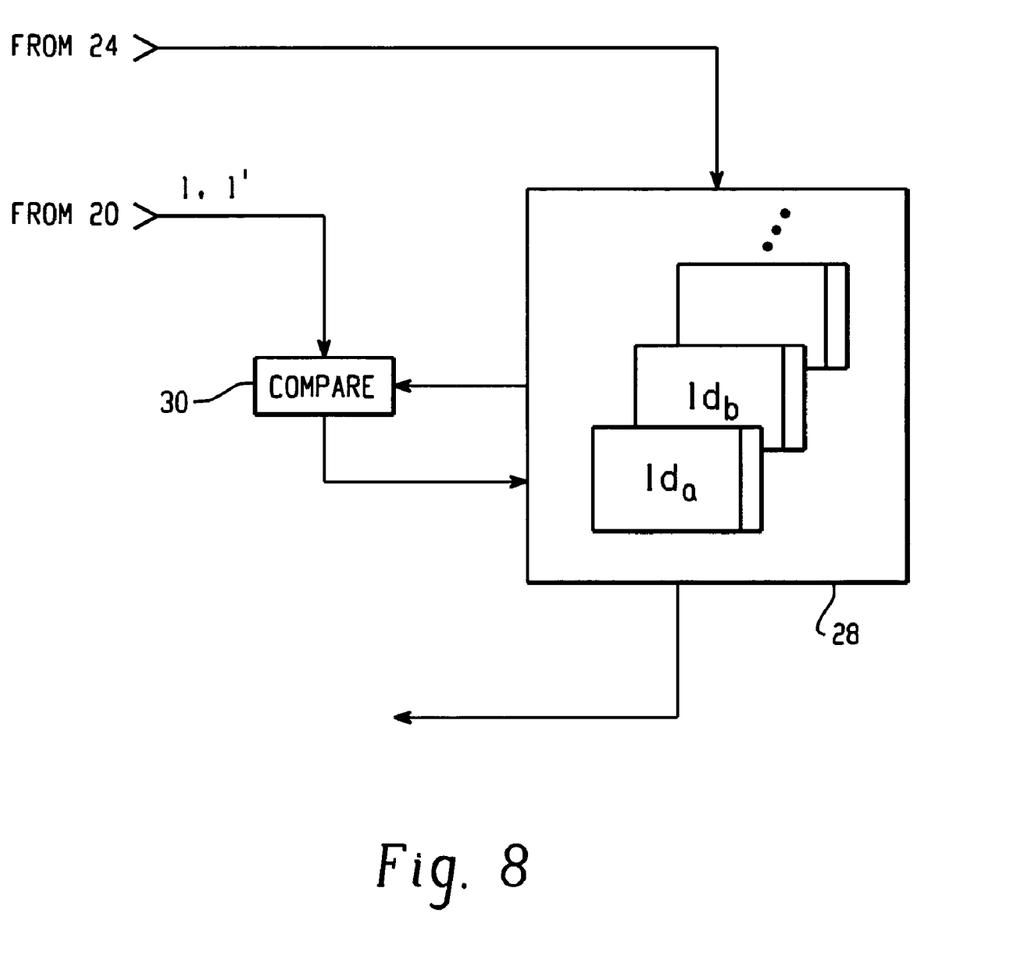

The expert system 28 basing on expert knowledge is in a most preferred embodiment construed and operated as explained with the help of FIG. 8. In the expert system 28 multiple digitized representations are provided, which after detailing have formerly resulted in satisfying shell and device manufacturing as approved by the involved individual and by the expert and with respect to devices applicable to the same body area as currently involved.

These formerly approved digitized representations 1da, 1db etc. are compared in a comparing step 30 with the actually treated digitized representation 1 or 1' and there is established by such comparison, which of the approved digitized representations 1d best matches with the actually treated digitized representation 1 or 1'. Once and as a result of this comparison 30 the best matching approved digitized representation is found, this best matching representation is addressed by an output of the comparing step 30 and the detailing data of detailing the respective approved digitized representation is output from the expert system 28 as suggestions for how the, actually treated digitized representation 1' of FIG. 2 should or could be detailed in detailing 22. If detailing is performed automatically, then such suggestion directly controls the detailing action. Thereby, and as shown in FIG. 8 the target information from target 24 is additionally input to expert system 28, as detailing may be completely different dependent whether e.g. a CIC is to be manufactured or an outside-the-ear hearing device OTE departing from the same digitized representation of outer ear and ear canal.

Looking back on FIG. 2, once detailing at step 22 has been performed and, as will further be addressed, dependent on the resulting detailed digitized representation 1*d* a shell and a device has been manufactured, which satisfy the respective individual as well as the expert, the respective digitized representation 1 or 1' with the detailing information according to 1*d* and preferably the target 24 information is input to the expert system 28 to update and improve its database.

Preferably both approaches, namely the approach of detailing based on rules, as outlined above, as well as detailing on the basis of "best match" are combined, whereby detailing suggestions based on the "best match" approach are preferably taken as first approximation for detailing, which approximation is then improved by considering the rules 26.

The expert system based on rules and knowledge 26, 28 is preferably continuously updated and improved by data of detailed digitized representations, which have resulted in devices, which optimally satisfy individual's needs. Obviously, devices and especially shells of devices, which turn out to be unsatisfying to the individual and which are e.g. returned by the individual due to bad detailing, are removed or are not entered with their respective digitized detailed representations to the expert systems 26, 28.

Figure 7:
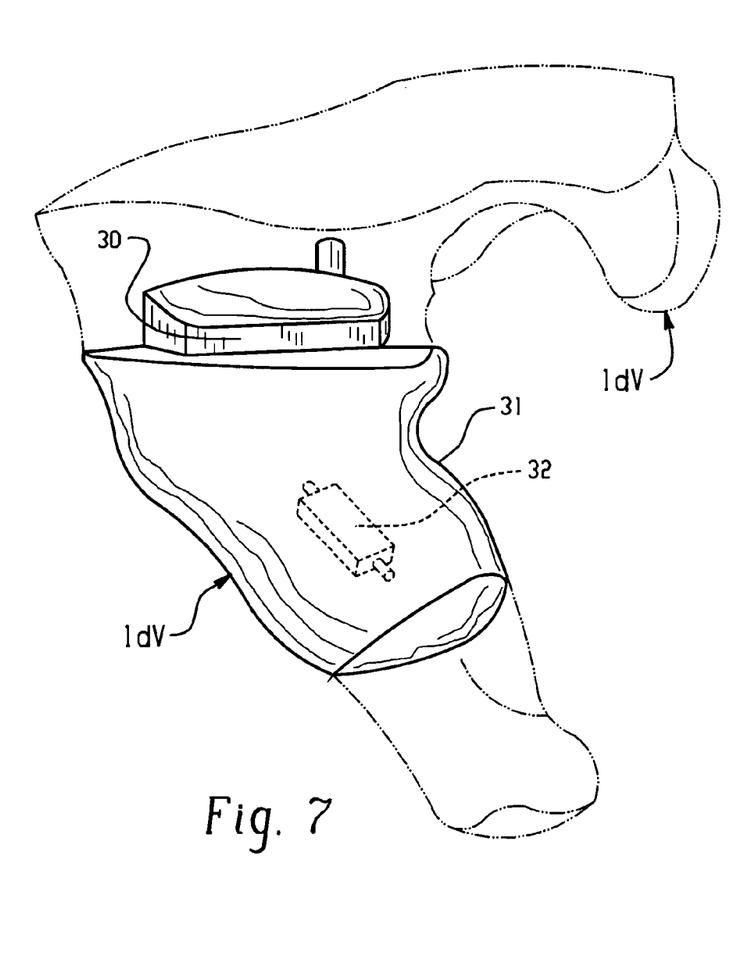
FIG. 7 departing from a digitized representation as shown in the FIGS. 4 to 6, visualization of an automatically or operator-interactively detailed target-specific digital representation with the target of manufacturing a CIC, and FIG. 8 schematically and by means of a signal-flow/functional block flowchart diagram, a preferred embodiment of applying a knowledge-based expert system for automatically generating detailing and/or suggestions how to detail a digitized representation of individual's body area of interest.

According to FIG. 2 the detailing step 22 results in a detailed digitized representation 1*d*. Thereat provision of modules for the device to be manufactured, namely the shell, possibly a face-plate, electronic modules, etc. has been considered. In FIG. 7 there is shown an example of a visualized detailed digitized representation 1*d*V combined with the target-specifically added modules as a face-plate 30, a shell 31, an electronic module 32.

As further shown in FIG. 2 in a most preferred embodiment the detailed digitized representation 1*d* is directly applied to a digitally controlled process for performing the shell-manufacturing step 36. Nevertheless, the detailed digitized representation 1*d* may also be applied for digitally controlling, in an overworking step 38, cast machining if there has been performed scanning 9 of a cast 7 to retrieve the digitized representation 1 and thus a cast 7 has already been used. After mechanically detailing a cast in step 38, in a mould-forming step 40 a mould is formed and therefrom, in shell-forming step 36, the shell. In a still further embodiment the detailed digitized representation 1*d* is applied for controlling digitally-controlled processing of a mould 40, if e.g. a material is to be used for manufacturing the shell in step 36, which is rather suited for a moulding technique than for a digitally controlled shaping technique.

Still another possibility is to manually overwork, in step 38, the cast or even, in step 40, the mould dependent from the information as gained from the detailed digitized representation 1*d*, e.g. via its visualization at monitor 13.

After performing shell-manufacturing according to one aspect of the present invention, under the further aspect in an assembling step 38 the device is assembled with the already produced shell-module from step 36.

Especially the step 20 of determining the characteristic features on the basis of pre-established rules 15 and/or a standard 17, the step 22 of automatic and preferably interactive detailing 22 in dependency of predetermined targets 24 and on the basis of a rule- and/or knowledge-based expert system 26, 28 are performed within a system according to the present invention, which comprises at least one storing unit for a data set representing a three-dimensional image and a processing unit, the input thereof being operationally connected to an output of the storing unit. The processing unit automatically generates a changed data set as performed by the automatic detailing action as was described.

The detailed digitized representation 1*d* is further preferably stored in a respective storing unit (not shown) at the device as assembled. This leads to the possibility that the individual carries all the information for manufacturing especially his device's shell with him. This information may be easily retrieved and irrespective, where the individual resides and may be transmitted e.g. via internet to a facility with shell-manufacturing installations so as to easily order a replacement shell.

Even if the individual is not completely satisfied by the momentarily worn device, he may, additionally to the above mentioned information, transmit his respective needs to the shell-manufacturing facility whereat, according to the option 11 of FIG. 2, the actually prevailing digitized representation may be subjected to additional checks and possibly redetailing according to the present invention.

The invention claimed is:

1. A method for manufacturing a body-worn device adapted to the shape of a body area of an individual, said method comprising the steps of:
   selecting one of a plurality of characteristic anatomical features of a shape of the body area as present at a standard of the body area;
   preparing a digitized three-dimensional representation of said characteristic anatomical feature;
   preparing a digitized three-dimensional custom representation of the body area of the individual;
   automatically determining a best-fitting location of said digitized representation of said characteristic anatomical feature at the digitized custom representation of the body area of the individual by comparing said digitized three-dimensional representation of said characteristic anatomical feature with and along said digitized three-dimensional custom representation of the body area of the individual;
   determining a detailing area oriented on said determined best-fitting location; and
   performing detailing of said digitized custom representation of the body area of the individual at said detailing area.

2. The method of claim 1, wherein said detailing comprises at least one of digitally cutting, surface treating, offsetting, fixing and relaxing a part of said digitized representation.

3. The method of claim 1, further comprising performing said localizing by automatically investigating said digitized representation under the constraint of predetermined geometrical rules.

4. The method of claim 1, further comprising the step of preparing said digitized custom representation by scanning a cast of said body area.

5. The method of claim 1, further comprising the step of preparing said digitized custom representation by scanning said body area.

6. The method of claim 1, wherein preparing said digitized custom representation comprises providing a digitized representation of said area which has already been applied for manufacturing a body-worn device.

7. The method of claim 1, further comprising the step of preparing said digitized custom representation by scanning a cast of said body area, and mechanically detailing said cast in dependency of said detailed digitized representation, thereby producing said shell from said detailed cast.

8. The method of claim 7, further comprising performing detailing of said cast by a digitally controlled treatment.

9. The method of claim 1, further comprising the step of producing a shell by a mould and producing said mould in dependency of said detailed digitized custom representation.

10. The method of claim 9, further comprising producing said mould by a digitally controlled process.

11. The method of claim 1, further comprising the step of producing a shell by means of a digitally controlled process, controlling said process comprising controlling said process by said detailed digitized custom representation.

12. The method of claim 1, further comprising performing automatically at least one of detailing and of providing at least one suggestion for said detailing.

13. The method of claim 12 wherein said step of providing automatically at least one of detailing and of at least one suggestion is performed on the basis of an expert system and at least one predetermined target to be achieved.

14. The method of claim 13, wherein said expert system is based on pre-established geometric rules and/or on recorded knowledge.

15. The method of claim 13 comprising updating said expert system in dependency of said detailed digitized representation, if latter is approved after producing said shell at the earliest.

16. The method of claim 12, wherein providing automatically at least one of detailing and of at least one suggestion comprises comparing said digitized representation with more than one digitized representation approved to be accurate, to find that approved digitized representation which best matches said digitized representation and generating said detailing and/or suggestion in dependency of said best matching digitized representation.

17. The method of claim 16, further comprising adding said digitized representation to said approved representations, if it is approved after producing said shell at the earliest.

18. The method of claim 1, further comprising checking accuracy of said prepared digitized custom representation and/or of said automatic determining by comparison of said digitized custom representation and/or at least one characteristic feature respectively with the standard digitized three-dimensional representation of said characteristic anatomical feature.

19. The method of claim 1, said device being a hearing device, said individual's body area comprising an ear canal, said at least one characteristic anatomical feature being at least one of:
   end of ear canal;
   entrance of the ear canal;
   medial axis of the ear canal;
   first canal bend;
   second canal bend;
   left ear canal;
   right ear canal; and
   horizontal orientation.

20. The method of claim 1, said individual's body area comprising individual's outer ear adjacent the ear canal, said at least one characteristic anatomical feature being at least one of:
   tragus;
   anti-tragus;
   inter-tragal notch;
   concha;
   crus;
   helix;
   left ear;
   right ear; and
   horizontal orientation.

21. The method of claim 1, wherein said device is a hearing device.

22. The method of claim 1, wherein said device is an in-the-ear hearing device.

23. The method of claim 1, wherein said device is an outside-the-ear hearing device.

24. The method of claim 1, wherein said device is a hearing aid device.

25. The method of claim 1, further comprising storing data for said producing said shell at said device.

26. A method for manufacturing a body-worn device adapted to the shape of a body area of an individual, said method comprising the steps of:
   selecting one of a plurality of characteristic anatomical features of a shape of the body area as present in a standard of the body area;
   preparing a digitized three-dimensional representation of said characteristic anatomical feature;
   preparing a digitized three-dimensional representation of the body area of the individual;
   on said digitized representation of the body area of the individual, automatically determining a best fitting location of said digitized representation of said characteristic anatomical feature at the digitized custom representation of the body area by at least one of:
      automatically applying predetermined rules for finding said at least one characteristic feature, and/or
      comparing said digitized custom representation of said body area with said digitized digital three-dimensional representation of said characteristic anatomical feature;
   determining a detailing area based on said automatically determined best-fitting location; and
   performing detailing of said area to be detailed.

27. A system for manufacturing a body-worn device adapted to the shape of a body area of an individual, said system comprising:
   means for selecting one of a plurality of characteristic anatomical features of a shape of the body area as present at a standard of the body area;
   means for preparing a digitized three-dimensional representation of said characteristic anatomical feature;
   means for preparing a digitized three-dimensional custom representation of the body area of the individual;
   means for automatically determining a best fitting location of said digitized representation of said characteristic anatomical feature at the digitized custom representation of the body area of the individual by comparing said digitized three-dimensional representation of said characteristic anatomical feature with and along said digitized three-dimensional custom representation of the body area of the individual;
   means for determining a detailing area oriented on said determined best-fitting location; and
   means for performing detailing of said digitized custom representation of the body area of the individual at said detailing area.

* * * * *

UNITED STATES PATENT AND TRADEMARK OFFICE
CERTIFICATE OF CORRECTION

| | | |
|---|---|---|
| PATENT NO. | : 7,555,356 B2 | Page 1 of 1 |
| APPLICATION NO. | : 10/406449 | |
| DATED | : June 30, 2009 | |
| INVENTOR(S) | : Samuel Hans Martin Roth et al. | |

It is certified that error appears in the above-identified patent and that said Letters Patent is hereby corrected as shown below:

Column 3, line 62-63, please replace the word "derailing" with -- detailing --.

Signed and Sealed this

Eighth Day of September, 2009

David J. Kappos
*Director of the United States Patent and Trademark Office*